United States Patent [19]

Usher et al.

[11] Patent Number: 6,156,534
[45] Date of Patent: Dec. 5, 2000

[54] SYNTHESIS OF β-LACTAM ANTIBACTERIALS USING SOLUBLE SIDE CHAIN ESTERS AND ENZYME ACYLASE

[75] Inventors: John J. Usher, East Syracuse; Guna Romancik, Jamesville, both of N.Y.

[73] Assignee: Bristol-Myers Squibb Company, Princeton, N.J.

[21] Appl. No.: 09/177,689

[22] Filed: Oct. 22, 1998

Related U.S. Application Data

[62] Division of application No. 08/895,640, Jul. 17, 1997, Pat. No. 5,922,907.
[60] Provisional application No. 60/022,622, Jul. 26, 1996.
[51] Int. Cl.$^7$ ........................................ C12P 37/00
[52] U.S. Cl. ........................... 435/43; 435/47; 435/46; 435/244
[58] Field of Search .......................... 435/47, 43, 46, 435/244

[56] References Cited

U.S. PATENT DOCUMENTS 4,340,672  7/1982  Kondo ........................................ 435/45

FOREIGN PATENT DOCUMENTS 640240   11/1993  Switzerland .
93/12250  6/1993  WIPO .
93/23164  11/1993  WIPO .

OTHER PUBLICATIONS

Fernandez–Lafuente et al., Synthesis of antibiotics (cephaloglycin) catalyzed by penicillin G acylase: Evaluation and optimizaiton of different synthetic approaches. Enzyme and Microbial Technology, 1996. vol. 19, pp. 9–14.

*Primary Examiner*—Irene Marx
*Attorney, Agent, or Firm*—David M. Morse; Prabodh I. Almaula

[57] ABSTRACT

Disclosed is a process for the synthesis of β-lactam antibacterials using soluble side chain esters in the presence of enzyme acylase. Also disclosed are novel esters useful as reactants in said process.

2 Claims, No Drawings

SYNTHESIS OF β-LACTAM ANTIBACTERIALS USING SOLUBLE SIDE CHAIN ESTERS AND ENZYME ACYLASE

This application is a divisional application of Ser. No. 08/895640 filed Jul. 17, 1997 now U.S. Pat. No. 5,922,907 claims priority from provisional U.S. application Ser. No. 60/022,622, filed Jul. 26, 1996, incorporated herein by reference in its entirety.

FIELD OF THE INVENTION

The present invention is directed to a process for the production of antibacterial β-lactams, namely penicillins and cephalosporins, in the presence of the enzyme, acylase, and a soluble ester as the acyl source. The invention is also directed to novel esters useful as reactants in said process.

DESCRIPTION OF RELATED ART

Japanese Patent Application Publication Nos. 47-25388, 47-29588, 48-26985, 48-35090, 48-99393, 49-14687, 49-36890, 49-48892, 49-75787, 49-134893 and 52-110896 teach processes for preparing penicillins or cephalosporins by reacting a methyl or ethyl ester of the acyl moiety to be introduced, with 6-aminopenicillanic acid or 7-aminocephalosporanic acid or derivatives thereof. The acyl source in these references is a lower alkyl ester and especially a methyl ester. Eiji Kondo, et al., U.S. Pat. No. 4,340,672, issued Jul. 20, 1982, discloses a process for preparing antibacterial β-lactams, that is penicillins and cephalosporins, by the action of an acylase on a penicillin or cephalosporin nucleus amine and an ester(1) of the following formula as the acyl source

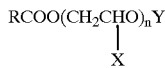

(I)

wherein RCO is an acyl group of penicillin or cephalosporin side chains; X is a hydrogen atom, lower alkyl group or hydroxy lower alkyl group; Y is a hydrogen atom or a lower alkyl group; and n is an integer from 1 to 20. The foregoing process uses the (poly)ethyleneglycol ester as the acyl source which is freely miscible with water as compared to known acyl sources, such as methyl esters, which have low solubility.

WO 92/01061, assigned to Novo Nordisk and published Jan. 23, 1992, relates to a process for the preparation of β-lactam derivatives by enzymatic acylation of the parent amino β-lactam with amides as acylating agents.

SUMMARY OF THE INVENTION

The present invention provides a novel process for preparing antibacterial β-lactams, that is penicillins and cephalosporins, by the action of an acylase on a penicillin or cephalosporin nucleus amine and an ester having the formula (II) as the acyl source

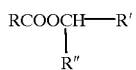

(II)

wherein RCO is a penicillin or cephalosporin side chain acyl group; R' is H or $CH_2X$ or CHXY; R" is H or $CH_2Y$ or CHXY and X and Y each are independently hydrogen, hydroxy, lower alkyl or hydroxy-lower alkyl.

DETAILED DESCRIPTION OF THE INVENTION

As used in the specification, unless otherwise indicated explicitly or by context, the acyl group represented by RCO is an acyl of natural or synthetic, penicillins or cephalosporins. The lower alkyl includes alkyl of 1 to 4 carbon atoms.

One aspect of the present invention provides a process for the production of β-lactam antibacterials by reacting an ester of the formula (II) with aminoazetidinone carboxylic acid of the formula (III) in the presence of acylase in an aqueous medium to produce the β-lactam antibacterial of the formula (IV):

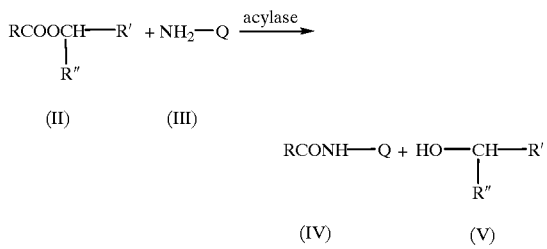

wherein RCO is an acyl group, $NH_2$—Q is an amino source and acylase is an enzyme of bacterial or fungal origin or obtained by recombinant methods. The substituents R' and R" are as defined above. The acyl group RCO can be straight, branched, cyclic, or partially cyclic lower alkanoyl or lower alkenoyl; monocyclic lower aralkanoyl, monocyclic aryloxylower alkanoyl, (O, N, or S)-heterocyclic-lower alkanoyl, (O, N, or S)-heterocyclic thio-lower alkanoyl, cyanoacetyl, cyanomethyl-thioacetyl, monocyclic arylglycyl, monocyclic cycloalkenylglycyl, monocyclicarylglycolyl, N-acyl-ariglycyl, monocyclicaryl-malonyl or arylsulfoalkanoyl, all above optionally having lower alkyl, aminomethyl, halogen, hydroxy, lower alkanoyloxy or lower alkoxy as a substituent, and preferably containing 1 to 15 carbon atoms.

The preferred RCO groups are D-phenylglycyl and 4-hydroxy-D-phenylglycyl which are well known as side chains of antibiotics such as cephalexin and amoxicillin.

The amino source $NH_2$—Q refers to the substituent on the 7-amino group or 6-amino group of known cephalosporin or penicillin antibiotics, Q having the formula (VI):

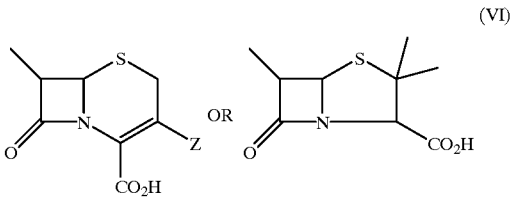

(VI)

wherein Z is hydrogen, halogen, lower alkyl of 1–3 carbon atoms, haloalkyl of 1–3 carbon atoms, $C_{2-4}$ alkenyl, a nucleophilic group or lower alkyl of 1–3 carbon atoms substituted by a nucleophilic group. The halogen atom is chlorine, bromine or iodine and the representative nucleophilic groups are disclosed in Japanese Patent Application Publication No. 49-81381.

The enzyme acylase can be of plant, animal, fungal or bacterial origin or obtained by recombinant methods. The bacterial or fungal acylases are especially important as far as production, efficiency, cost and stability are concerned.

Representative bacteria or fungi for the acylase source include strains of microorganisms belonging to, for example, genera Acetobacter, Achromobacter, Aeromonas, Alkaligenes, Arthrobacter, Brevibacterium, Beneckea, Bacillus, Corynebacterium, Escherichia, Flavobacterium, Gluconobacter, Kluyvera, Microbacterium, Micrococcus, Nocardia, Proteus, Pseudomonas, Rhodopseudomonas, Spirillum, Staphylococcus, Xanthomonas, Aphanociadium or Cephalosporium, or natural or artificial mutants or variants of them capable of producing acylase for the reaction of this invention. Such strains include those described in, for example, *Advances in Applied Microbiology*, Volume 20, page 217 (1976), or natural or artificial mutants of them available for the reaction of this invention. An especially useful enzyme is penicillin G amidase which can be obtained from *Escherichia coli* by methods which are well known in the art. It can also be obtained by use of recombinant *E. coli* containing the penicillin G amidase gene with a tac promoter by methods which are well known in the art. This method is preferred since it makes available large quantities of the enzyme suitable for the manufacturing process.

The aminoazetidinone carboxylic acid of formula (III) can be used as water soluble alkali metal salts, such as sodium, lithium and potassium, or as an ester, such as methanesulfonylethyl ester or acetonyl ester. The aminoazetidinones of formula (III) and its salts or esters are known compounds and can be prepared by known methods.

The esters of formula (II) can be prepared by known methods, that is, by reaction of an acid RCOOH with a diol or triol or polyol of the formula (V):

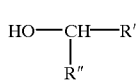

(V)

wherein RCO, R' and R" are as defined above. The esterification reaction can be by dehydration under acid catalyzed conditions or by means of acid halide or by ester exchange reactions. The RCOOH and the diol, triol or polyol are known compounds or can be obtained by methods which are well known in the art.

Another aspect of the invention provides the ester R—COO—CH$_2$—CH$_2$—OH wherein R is D-phenylglycyl or 4-hydroxy-D-phenylglycyl. These esters are novel and important reactants in the process of the invention because they provide yields of over 90% of the final products. These esters are prepared by known methods.

A preferred embodiment of the present invention is a process for preparing antibacterial β-lactams, that is, cefprozil, cefadroxil and amoxicillin by the action of penicillin G amidase on penicillin or cephalosporin amines of the following formula (VII):

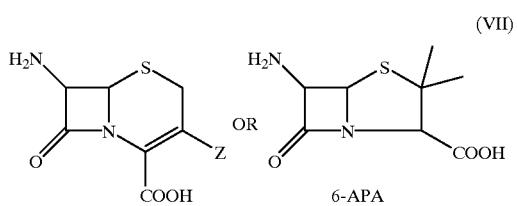

(VII)

wherein Z is methyl (in 7-ADCA) or I-propenyl (in 7-PACA, the cefprozil nucleus) group and an ester of the formula (VIII):

R—COO—CH$_2$—CH$_2$—OH (VIII)

wherein R is 4-hydroxy-D-phenylglycyl. The penicillin or cephalosporin amines of the formula (VII) are known compounds and can be obtained by methods well known in the art. The ester of formula (VIII) can be obtained by reacting RCOOH wherein R is defined as above with ethylene glycol. The compound RCOOH and ethylene glycol are commercially available.

The process of the invention is carried out by preparing a solution containing ester, cephalosporin or penicillin amine and the enzyme without a buffer at room temperature. This solution is prepared by dissolving the ester in water and adding ammonium hydroxide until a pH of 7.5 is reached. Then the penicillin or cephalosporin amine is added to the ester solution and the pH again adjusted to 7.5 with ammonium hydroxide. The mixture is then cooled to 5–15° C. and the solid enzyme is added to it. During this time, the pH falls about 0.6 units and is not maintained at 7.5. The reaction mixture is then analyzed by high pressure liquid chromatography, for example on a C18 reversed phase column, 5 cm×4.6 mm, 5 μm spherosorb ODS2. The final product is obtained in a yield of 90–99%.

The process of this invention gives the final antibacterial β-lactam in the usual yield of over 90% and sometimes over 95% and occasionally over 99%. The yield obtained by simple alkyl esters, such as methyl are usually in the range of 70 to 90%. Because of the high yield of the final antibiotic obtained by the present process, the process is very useful for the manufacture of penicillin or cephalosporin antibiotics.

A typical reaction mixture contains 5–35% of the acyl source (VIII) (preferably 8–12%) and 2–20% of the amine source (VII) (preferably 2–5%). The enzyme can be present in a soluble or insoluble form, but preferably the enzyme is present in the form of an insoluble immobilized preparation. This preparation has advantages, such as improved stability of the enzyme and also relative ease of removal of immobilized enzyme from reaction mixtures as a first step in the isolation of the antibiotic.

The invention is illustrated but in no way limited by the following Examples:

EXAMPLE 1

Synthesis of cefprozil from (VII) using immobilized recombinant penicillin G amidase as the enzyme and hydroxyethyl ester of 4-hydroxy-D-phenyiglycine prepared by acid catalyzed reaction as the acyl source A mixture of 4-hydroxy-D-phenylglycine (10 g), ethylene glycol (15 ml) and concentrated sulphuric acid (5 ml) was stirred for 18 hours at 55° C. under anhydrous conditions. The solution was cooled, and then ice (10 g) was added to it, and the pH was adjusted to 1.0 with 10 N—NH$_4$ OH (4.5 ml) giving 40 ml of solution of hydroxyethyl ester.

The enzyme mixture of 20 ml containing 10% ester, 4% (VII), and 8% enzyme (equivalent to 32 IU/ml of enzyme) was made up without buffer as follows:

The above prepared ester solution (6.9 ml) was mixed with water (2 ml) and adjusted to pH 7.5 with 10 N—NH$_4$OH. Then the compound (VII) (0.8 g) was added to it and the pH adjusted to 7.5 with 1 N-NH$_4$0H and the volume to 18.4 ml. Then the mixture was cooled to 5–15° C. and solid enzyme (1.6 g; 640 IU) was added to it. The pH was not maintained at 7.5 and fell about 0.6 units during the reaction. The reaction mixture was analyzed by HPLC on a C18 Reverse Phase column 5 cm×4.6 mm, 5 μm spherosorb ODS2. The mobile phase was 10% acetonitrile/0.3% H$_3$PO$_4$©2 mil/minute with 215 nm detection. The isomers of cefprozil appeared at 2.9 minutes (cis) and at 5.1 minutes (trans). The final product was obtained with a maximum yield of 92–96%. The whole experiment was completed in 25–50 minutes.

EXAMPLE 2
Synthesis of cefprozil from (VII) using immobilized recombinant penicillin G amidase as the enzyme and purified hydroxyethyl ester of 4-hydroxy-D-phenylglycine as the acyl source The purified ester was prepared by the reaction of the Dane salt of 4-hydroxy-D-phenylglycine with bromoethanol and was obtained as a pure crystalline hydrochloride salt.

The reaction mixture of 20 ml containing 12.5% ester, 4% (VII), and 8% enzyme (equivalent to 24 IU/ml of enzyme) was prepared as follows:

The purified ester (2.5 g), prepared as above, was mixed with water (9 ml) and adjusted to pH 8.0 with concentrated $NH_4OH$ to give a solution. The compound (VII) (0.8 g) was added to the solution and the pH of the solution adjusted to 6.76 with $2M—H_2SO_4$ and the volume to 18.4 ml. This solution was cooled to 15° C. and then solid enzyme (1.6 g; 480 IU) was added to it. The pH was not maintained and fell about 0.6 units during the reaction. The final product was obtained in a maximum yield of 99%. The area percent of unreacted (VII) fell to 0.7%. The experiment was completed in twenty-five minutes.

EXAMPLE 3
Synthesis of cefadroxil from 7-ADCA using Boehringer penicillin G amidase as the enzyme and hydroxyethyl ester of 4-hydroxy-D-phenylglycine prepared by acid catalyzed reaction as the acyl source The ester was prepared as in Example 1. The experiment was repeated as in Example 1 but at 15° C. and using 1.6 g of the Boehringer enzyme. The reaction mixture was analyzed by HPLC on a Merck column, 250-4, LiChrosorb RP-18 (10 μm), with 10% acetonitrile/1% $NH_4H_2PO_4$ as mobile phase run at 1.3 ml/minute with 280 nm detection. The product was obtained with a maximum yield of ~95%. The experiment was completed in 35 minutes.

EXAMPLE 4
Synthesis of amoxicillin from 6-APA using Boehringer penicillin G amidase as the enzyme and hydroxyethyl ester of 4-hydroxy-D-phenylglycine prepared by acid catalyzed reaction as the acyl source A mixture of volume 20 ml containing 12% ester, 3% 6-APA, and 8% enzyme was prepared as follows:

A solution of the ester (prepared as in Example 1, 8.3 ml) was mixed with water (2 ml) and adjusted to pH 7.5 with 10 $N—NH_4OH$. Then the compound 6-APA (0.6 g) was added to the solution and the pH adjusted to ~7.0 with 1 N ammonium hydroxide to a volume to 18.4 ml. Then the solution was cooled to 20° C. and Boehringer enzyme (1.6 g) was added to it. This solution was analyzed by HPLC on a C18 Reverse Phase column 5 cm×4.6 mm, 5 μm spherosorb ODS 2. The mobile phase was 2.5% acetonitrile/0.025M $NaH_2PO_4$ to pH 3.5 with $H_3PO_4$ run@1 ml/minute with 215 nm detection. The final product was obtained in a yield of 90–95% in 160 minutes.

What is claimed is:

1. A process for producing antibiotic cefprozil, cefadroxil or amoxicillin, comprising reacting:

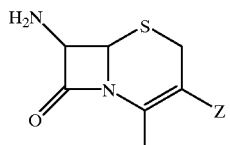

OR

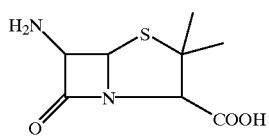

wherein Z is methyl or 1-propenyl group with an ester of the formula

$$R—COO—CH_2—CH_2—OH$$

wherein R is 4-hydroxy-D-phenylglycyl in the presence of the enzyme, penicillin G amidase to produce cefprozil, cefadroxii or amoxicillin.

2. The process of claim 1, wherein the enzyme is immobilized recombinant penicillin G amidase.

* * * * *